(12) United States Patent
Paur et al.

(10) Patent No.: US 10,527,482 B2
(45) Date of Patent: Jan. 7, 2020

(54) DEVICE FOR MEASURING SUPERFINE PARTICLE MASSES

(71) Applicant: KARLSRUHER INSTITUT FUER TECHNOLOGIE, Karlsruhe (DE)

(72) Inventors: Hanns-Rudolf Paur, Karlsruhe (DE); Sonja Muelhopt, Karlsruhe (DE); Christoph Schlager, Elzach (DE)

(73) Assignee: KARLSRUHER INSTITUT FUER TECHNOLOGIE, Karlsruhe (DE)

( * ) Notice: Subject to any disclaimer, the term of this patent is extended or adjusted under 35 U.S.C. 154(b) by 386 days.

(21) Appl. No.: 15/536,666

(22) PCT Filed: Dec. 17, 2015

(86) PCT No.: PCT/EP2015/002546
§ 371 (c)(1),
(2) Date: Jul. 11, 2017

(87) PCT Pub. No.: WO2016/096137
PCT Pub. Date: Jun. 23, 2016

(65) Prior Publication Data
US 2018/0128671 A1    May 10, 2018

(30) Foreign Application Priority Data
Dec. 17, 2014    (DE) .......... 10 2014 118 846

(51) Int. Cl.
*G01G 7/06* (2006.01)
*G01N 1/22* (2006.01)
(Continued)

(52) U.S. Cl.
CPC ............. *G01G 7/06* (2013.01); *B01L 99/00* (2013.01); *G01N 1/2208* (2013.01);
(Continued)

(58) Field of Classification Search
CPC .......... G01N 1/2208; G01N 2015/0065; G01N 2015/0046; G01N 2015/0038
See application file for complete search history.

(56) References Cited

U.S. PATENT DOCUMENTS 3,561,253 A * 2/1971 Dorman ............... G01N 29/036
73/24.03
2002/0124632 A1    9/2002 Reiter et al.
(Continued)

FOREIGN PATENT DOCUMENTS

DE     198 01 763 A1    7/1999
DE     198 01 763 C2    10/1999
(Continued)

OTHER PUBLICATIONS

M. Savi et al.: "A Novel Exposure System for the Efficient and Controlled Deposition of Aerosol Particles onto Cell Cultures", Environmental Science & Technology, vol. 42, No. 15, pp. 5667-5674 (2008).
(Continued)

*Primary Examiner* — Dominic E Hawkins
(74) *Attorney, Agent, or Firm* — Norman B. Thot

(57) ABSTRACT

A device for measuring superfine particles masses includes an exposure system with at least two measurement chambers having an identical geometry. Each measurement chamber has a deposition surface for the superfine particles which each have an aerosol feed line. The aerosol feed line has an outlet region to feed an aerosol onto the deposition surface, a means for generating a potential difference between the superfine particles in the aerosol and the deposition surface, and a grid arranged above the deposition surface. The outlet region has a widened outlet cross section having a constant distance from the deposition surface. At least one deposition surface is arranged on a piezoelectric crystal as a superfine balance. A first potential corresponding to a ground potential
(Continued)

Figure 1:
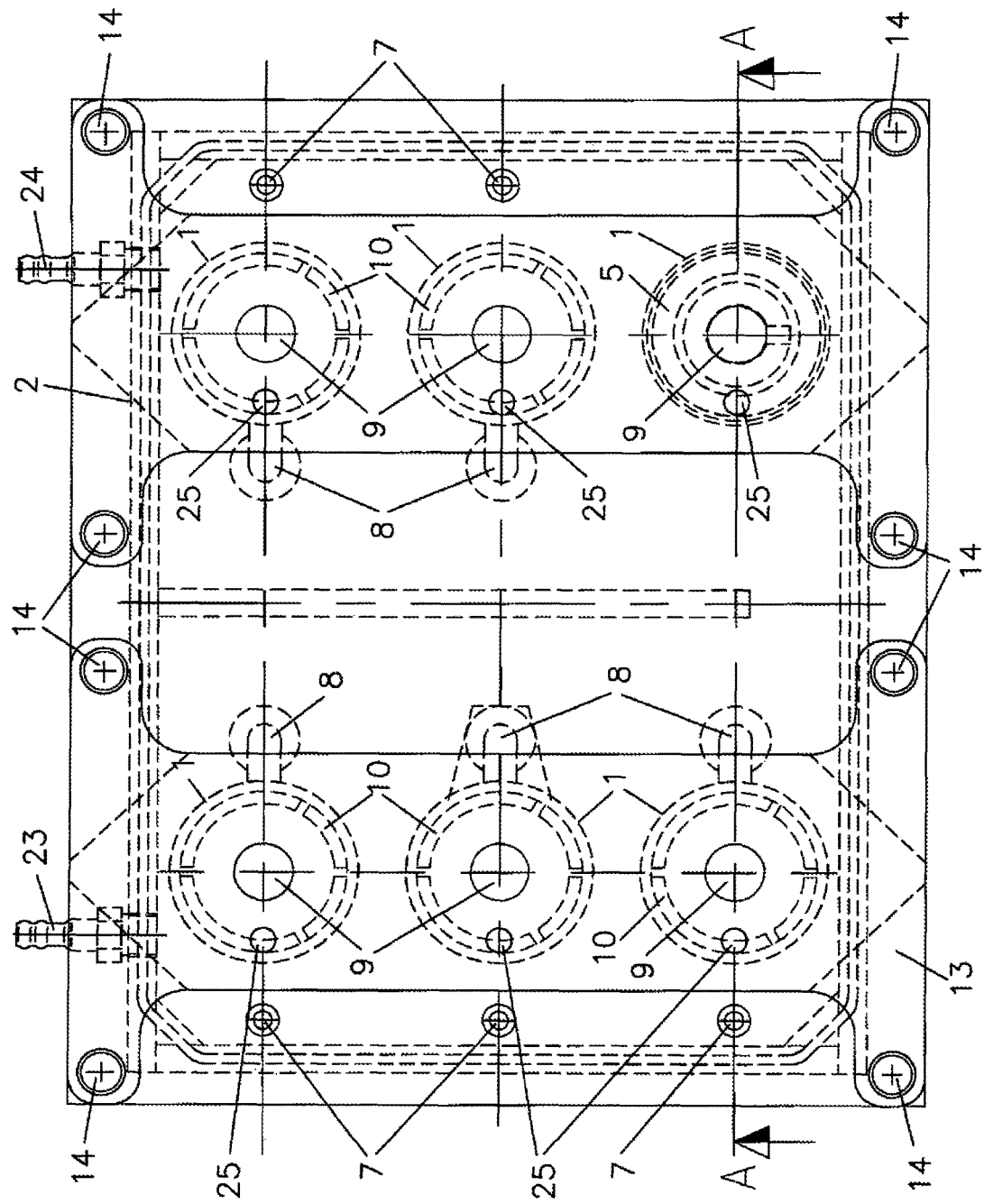

is present at each deposition surface. A second potential having a potential difference of at least 200 V in relation to the first potential is present at each grid.

11 Claims, 5 Drawing Sheets

(51) Int. Cl.
　　*G01N 15/06*　　　(2006.01)
　　*B01L 99/00*　　　(2010.01)
　　*H01L 41/04*　　　(2006.01)
　　*G01N 15/00*　　　(2006.01)
　　*G01N 5/02*　　　(2006.01)

(52) U.S. Cl.
　　CPC ......... *G01N 15/0606* (2013.01); *H01L 41/04* (2013.01); *B01L 2300/10* (2013.01); *B01L 2300/16* (2013.01); *B01L 2300/18* (2013.01); *G01N 5/02* (2013.01); *G01N 2015/0038* (2013.01); *G01N 2015/0046* (2013.01); *G01N 2015/0065* (2013.01)

(56) References Cited

U.S. PATENT DOCUMENTS

| | | | |
|---|---|---|---|
| 2010/0083737 A1* | 4/2010 | Paur | G01N 5/02 73/24.03 |
| 2012/0251594 A1* | 10/2012 | Longest | A61K 9/008 424/400 |
| 2012/0274933 A1 | 11/2012 | Doucette et al. | |

FOREIGN PATENT DOCUMENTS

| | | |
|---|---|---|
| DE | 100 61 976 A1 | 6/2001 |
| DE | 10 2007 013 938 A1 | 9/2008 |
| EP | 1 174 496 A2 | 1/2002 |

OTHER PUBLICATIONS

DIN CEN ISO/TS 27687: "Nanotechnologies—Terminology and definitions for nano-objects—Nanoparticle, nanofibre and nanoplate", English Version of DIN CEN ISO/TS 27687, pp. 1-14 (Nov. 2008).
http://www.cultex-laboratories.com/wp-content/uploads/2014/02/psp-cultex-systems.pdf, Cultex Laboratories GmbH, pp. 1-12 (Aug. 18, 2014).

* cited by examiner

DEVICE FOR MEASURING SUPERFINE PARTICLE MASSES

CROSS REFERENCE TO PRIOR APPLICATIONS

This application is a U.S. National Phase application under 35 U.S.C. § 371 of International Application No. PCT/EP2015/002546, filed on Dec. 17, 2015 and which claims benefit to German Patent Application No. 10 2014 118 846.2, filed on Dec. 17, 2014. The International Application was published in German on Jun. 23, 2016 as WO 2016/096137 A1 under PCT Article 21(2).

FIELD

The present invention relates to a device for measuring superfine particle masses, for example, on a bioassay.

BACKGROUND

Devices for measuring superfine particle masses serve to record and/or analyze immissions from aerosols or dusts in general. Of interest first of all in this connection are the purely physical deposition kinetics on particular surfaces (deposition surfaces) by adsorption. Substances can at the same time also diffuse into the surface from the aerosols or dusts, i.e., be taken up and embedded (absorption) as part of a physical diffusion process. It is also possible for chemical and physical interactions of the superfine particles on or in the deposition surfaces to be recorded by these devices and to be quantified by additional morphological, physical or chemical analysis methods of a known type.

An important area of use of the aforementioned devices are also in vitro analyses of fine-dust depositions or of biochemical or biophysical interactions on bioassays, i.e., on biological or biologically active surfaces. Especially in the case of a toxicological assessment of atmospheric dust exposures and atmospheric noxiant exposures, for example, at contaminated work areas, in traffic, or in industrial plants, such analyses are a supplement to epidemiological studies (with statistical data) or in vivo analyses on living individuals (e.g., with animal experiments) that is useful and preferred due to ethical considerations.

Immissions analysis is particularly important in the case of so-called superfine particle exposures. Superfine particles, which also include nanoparticles, refer to particles having diameters below 10 μm, i.e., from a few nanometers to at most one micrometer. Standardized in DIN ISO/TS 27687 are, for example, fine dust (e.g., PM10=particle diameter less than 10 μm) and ultrafine dust. A nanoparticle is therefore a nanoobject having all three outer dimensions on the nanoscale from 1 to 100 nm. Superfine particles, with their very large ratio of surface to mass, often have a property profile and reaction behavior which is completely different compared to larger particles or solid bodies and which has not yet been completely studied and is thus unknown.

DE 100 61 976 A1 describes a device for measuring superfine particle masses comprising an exposure system having a measurement chamber having a deposition surface for particles on a piezoelectric crystal, each deposition surface having an aerosol feed line directed thereto for feeding an aerosol onto the deposition surface.

In vitro investigations relating to the measurement of superfine particle masses and also their toxicological effects on living organisms often utilize biological model structures such as, for example, cell cultures on a corresponding cultivation support structure such as, for example, a Petri dish or, in the case of bacterial cultures, a nutrient medium or membrane culture inserts having pores in relation to the lower compartment. The structures are exposed as open layer to the aerosol or to a suspension of a carrier fluid (gas or liquid) and the superfine particles.

DE 198 01763 C2 describes a culture device for the cultivation of cells or tissue components in which the cell cultures are grown on porous membranes in culture inserts. For the aforementioned in vitro investigations, the nutrient solution on the upper side of the planar cultures is removed for the application of an aerosol, whereas the space below the membrane is continuously flushed with fresh nutrient medium for cell sustenance and to avoid an accumulation of toxic metabolic products. The system has already established itself in many areas of inhalation research such as, for example, for studying diesel soot and cigarette smoke.

EP 1 174 496 A1 also describes a device to cultivate biological cultures having a gaseous fluid on the top side and a liquid on the bottom side combined with a computational dose determination.

The in vitro investigations known to date are, however, solely based on time-integral measurements. The cell cultures are, as are the aforementioned in vivo investigations, only examined at intervals, i.e., only after expiration of a particular test duration. In many cases, fluctuations in an aerosol immission and their temporary biochemical effects on a cell culture cannot be comprehended or can only be comprehended very imprecisely, for example, on the basis of individual tests.

DE 10 2007 013 938 A1 describes a device for measuring superfine particle masses with an exposure system having at least two measurement chambers each having a deposition surface of identical geometries and each having an aerosol feed line directed to the respective deposition surface. The design involves at least one of the deposition surfaces on a piezoelectric crystal as a superfine balance and other deposition surfaces without piezoelectric crystal. An electrical field between aerosol feed line and deposition surface is also proposed to increase the efficiency of deposition. The recommendation is to minimize the difference in electrical potential between any ionized superfine particles in the aerosol and the aerosol feed line.

Cultex Laboratories GmbH, Hanover, also supplies a culture chamber in which an aerosol is charged by a corona on an input side and conducted onto cell cultures with an applied electric potential.

Savi et al. describes a similar concept (Savi M., Kalberer M., Lang D., Ryser M., Fierz M., Gaschen A., Rička J., Geiser M.; *A novel exposure system for the efficient and controlled deposition of aerosol particles onto cell cultures; Environmental Science and Technology* 42 (2008) 5667-5674) of a passive grid over the deposition surface for the homogenization of the electrical field.

The only currently-known devices are therefore devices to measure superfine particle masses with electrostatic deposition, in which devices the deposition surface is, as the electrode, at a voltage level (for example a high voltage in the kV range). If the deposition surface is provided with a piezoelectric crystal as a superfine balance for a QCM measurement (QCM=Quartz Crystal Microbalance), the superfine balance must disadvantageously also be controlled at the stated voltage level. In relation thereto, the stated voltage level is applied to the above-lying measurement electrode of the piezoelectric crystal and thus corresponds to the potential at the cell culture. So as not to significantly alter the QCM measurement, the principle of which is based on the change in natural frequency in the excited piezoelectric crystal, the necessary voltage difference of a few volts between measurement electrode and the second annular electrode of the piezoelectric crystal should be raised altogther by 1000 volts, i.e., the annular electrode to 1000 volts and the measurement electrode to, for example, 1010 volts. However, the realization of such a concept requires novel oscillators and an inconvenient complex frequency analysis.

Superfine dust or nanoparticles are distinguished by a large specific surface area. This significantly favors a strong adhesion of these particles to planar surfaces, such as the stated deposition surfaces, predominantly by van der Waals forces. Further adhesion mechanisms such as, for example, bondings or surface voltage effects may additionally have an effect, but take a backseat and are negligible in the present case for fine dusts or nanoparticles.

SUMMARY

An aspect of the present invention is to further improve the last-mentioned device for measuring superfine particle masses.

In an embodiment, the present invention provides a device for measuring a mass of superfine particles. The device includes an exposure system comprising at least two measurement chambers which have an identical geometry. Each of the at least two measurement chambers comprises a deposition surface for the superfine particles, and an aerosol feed line directed to each deposition surface. The aerosol feed line comprises an outlet region for feeding an aerosol onto the deposition surface, a means for generating a potential difference between the superfine particles in the aerosol and the deposition surface, and a grid arranged above the deposition surface. The grid is configured to completely span the outlet region. The outlet region comprises a widened outlet cross section which is configured to have a constant distance from the deposition surface over its entire circumference so as to form a circumferential gap nozzle and so that a suction volume is arranged concentrically around the aerosol feed line. At least one deposition surface is arranged on a piezoelectric crystal as a superfine balance. A first potential corresponding to a ground potential is present at each deposition surface. A second potential having a potential difference of at least 200 V in relation to the first potential is present at each grid so that an electrical field spreads between a respective grid and a respective deposition surface.

BRIEF DESCRIPTION OF THE DRAWINGS

The present invention is described in greater detail below on the basis of embodiments and of the drawings in which:

FIG. 1 shows a top view of one embodiment having six exposure chambers;

FIG. 2 shows a sectional representation of the device (as per FIG. 1 at the line indicated by A-A);

FIG. 3 shows a sectional representation of a possible design of an exposure chamber with deposition surface, an aerosol feed line with grid, with only the grid being under voltage;

FIG. 4 shows a sectional representation of a possible design of an exposure chamber with deposition surface, an aerosol feed line with grid, with only the grid being under voltage;

FIG. 5 shows a sectional representation of an embodiment of an aerosol feed line with grid, with only the grid being under voltage;

FIG. 6 shows a sectional representation of a further possible design of an exposure chamber with deposition surface, an aerosol feed line with grid, with the grid and the aerosol feed line being under voltage; and FIG. 7 shows a sectional representation of a further possible design of an exposure chamber with deposition surface, an aerosol feed line with grid, with the grid and the aerosol feed line being under voltage.

DETAILED DESCRIPTION

The present invention provides a device for measuring superfine particle masses which are designed for investigations relating to immission of superfine particles on deposition surfaces, for example, via sedimentation, diffusion, adsorption or absorption or other physical or chemical bonding.

The present invention proposes a device to measure superfine particle masses in exposure chambers which each have an aerosol feed line and a deposition surface, in which an electrical field is generated in the exposure chamber for an electrostatically assisted deposition. The deposition surfaces thereby form a field electrode and a potential of not more than 50 volts in relation to the ground potential is present at each of the deposition surfaces. This approach has the following advantages over known solutions:

A voltage level close to the ground potential on deposition surface and at the piezoelectric crystal; and No need for complicated electronics and data acquisition.

The above is achieved based on a device for measuring superfine particle masses comprising an exposure system having at least two measurement chambers (exposure chambers) of identical geometries, each comprising a deposition surface for particles, each deposition surface having an aerosol feed line which is directed thereto and which has an outlet region for the feeding of an aerosol onto the deposition surface. At least one of the deposition surfaces is formed on a piezoelectric crystal as superfine balance. This involves positioning the at least one deposition surface on a piezoelectric crystal or connecting it to a piezoelectric crystal in a direct manner or via a waveguide component.

In an embodiment, at least one of the deposition surfaces is not arranged on a piezoelectric crystal or is not connected to such a crystal, i.e., the deposition surface is not a superfine balance. The device thus comprises deposition surfaces with and without a piezoelectric crystal.

In an embodiment, only one of the deposition surfaces can be positioned on a piezoelectric crystal or be connected to a piezoelectric crystal in the aforementioned manner, whereas other deposition surfaces do not have a piezoelectric crystal.

In an embodiment, all deposition surfaces can be implemented on, in each case, a piezoelectric crystal as superfine balances. This design additionally allows comparative determinations of mass on the piezoelectric deposition surfaces and thus also an early identification of defective exposure chambers (quality control).

A deposition surface with piezoelectric crystal, designed as superfine balance, does not occupy a different deviating position in the exposure chamber compared to other deposition surfaces without piezoelectric crystal. This means that it is not only possible to carry out during a test period a mass determination of the superfine particle masses bound to the deposition surface, but it is also possible to estimate the superfine particle masses on the other deposition surfaces owing to the identical arrangements in the exposure chamber, and thus owing to an assumable transferability to the other exposure chambers of identical geometries.

In this connection, the mass determination can, via the deposition surfaces designed as superfine balance, take place continuously during the test period or as one or more individual measurements, with the control of the piezoelectric crystal and the recording of data of the piezoelectric crystal, for example, being under computer control.

A recording or method steps are therefore envisaged which record an imission of the particles on deposition surfaces not only in an integral manner, but also in a time-resolved manner. The deposited quantity of immitted particles is thereby recorded in an ongoing and, for example, also in a quantitative manner. The course of a deposition can thus be monitored online. The thereby achievable advantage of such an online recording is not only the prompt recording of the particle deposition on the deposition surfaces, but also the prompt processing of these deposition rates as measured values for test-related control commands, for example, for test-management manipulations, alarm systems, or for supplementary measurements as well as for safety-related measures.

The deposition efficiency on the deposition surfaces can be influenced by a means for generating a potential difference between the particles in the gas and the deposition surfaces.

What is proposed via the above means for generating a potential difference between the particles in the gas and the deposition surfaces is to apply to each of the deposition surfaces a uniform potential of not more than 50 volts, for example, not more than 20 volts, for example, 10 volts, in relation to the ground potential. The deposition surfaces can, for example, be directly connected to the ground potential (grounded, neutral). The deposition surface can, for example, be situated on an electrode or is formed by the electrode itself. It forms a measurement electrode at which the stated uniform potential, for example, the ground potential, is present. In an embodiment, the measurement electrode simultaneously serves as one of the two control electrodes for exciting the piezoelectric crystal. In an embodiment, the measurement electrode is arranged as annular electrode around the deposition surface.

It is also optionally proposed to electrically connect the deposition surfaces to one another in order to provide a common potential on the deposition surfaces.

The aforementioned feature additionally comprises one grid for each deposition surface, which grids are arranged above the respective deposition surfaces. A potential having a potential difference of at least 200 volts, for example, between 500 and 10,000 volts, and, for example, between 1,000 and 5,000 volts, in relation to the potential of the deposition surfaces, is present at each of the grids, with an electrical field spreading between the grids and the respective deposition surfaces.

Over its entire area, the grid can, for example, have an identical mesh width (for example, between 0.5 and 10 mm, for example, between 1 and 5 mm) and a constant strand width.

In an embodiment, electrical insulation between aerosol feed line and grid is envisaged. The aerosol feed line or at least the contact surface toward the aerosol alternatively consists of an electrically nonconductive material or an electrically nonconductive coating. In this connection, the aforementioned potential difference can, for example, be applied to the grid via a cable connection. When a positive voltage is present at the grid, negative charged particles can, for example, be deposited at the contact surface and/or the grid. In contrast, the positively charged particles are conducted to the deposition surface in an increased manner, it thus being possible to achieve an overall dose increase.

In an embodiment, an aerosol feed line having at least an electrically conductive contact surface toward the aerosol without the aforementioned insulation can, for example, be provided. The grid and the aerosol feed line thus have the same electrical potential and can, for example, be electrically insulated with respect to the surrounding components of the device by an electrically nonconductive component (insulation or electrically nonconductive component of the aerosol feed line).

The aforementioned embodiment of deposition surfaces and grids allows the spreading of the stated electrical field and, at the same time, an advantageous electrical decoupling of the piezoelectric crystal from higher voltages, for example, the stated potentials present at the grids or potential differences in relation to the deposition surfaces. A direct coupling of the deposition surfaces to the ground potential additionally allows a direct diversion of possible voltage pulses and thus an additional safeguard against interference voltages.

To generate identical or similar deposition conditions and thus deposition kinetics over the entire deposition surface, the grids span the respective outlet regions, for example, completely and/or in parallel to the deposition surfaces.

The distance between deposition surface and grid is between 0.5 and 10 mm, for example, between 1 and 3 mm (1 mm would be ideal, though an improved short-circuit resistance is achievable with 2-3 mm), giving an electrical field strength of, for example, 300-700 V/cm for the aforementioned potential differences.

In an embodiment, a device or method steps for the ionization of these superfine particles masses in the aerosol are provided, for example, already before entry into the aerosol feed line. The ionization can, for example, be achieved electrically or photonically, even radioactively in individual cases, it being possible to selectively control or quicken the ionization by additives which are to be added to the aerosol and which, for example, act as charge carriers. To avoid a premature deposition of superfine particles, for example, in the aerosol feed line, the electrical potential difference between ionized superfine particles in the aerosol and the aerosol feed line should be minimized. To increase the deposition rates of the ionized particles on the deposition surfaces, an electrical field is then set between the deposition surfaces and the outlet region of the aerosol feed line, for example, in the annular gap.

If the superfine particle masses are composed of multiple different particle fractions, they can, for example, be separated in two different ways via the aforementioned selective ionization. Selectively ionized particle fractions can be deposited in an electrical field before entry into the device. Deposition of the ionized particle fractions can be selectively significantly increased by application of the aforementioned electrical field between deposition surface and outlet region.

In the case of the aforementioned measurement chambers (exposure chambers) of identical geometries, the deposition surfaces are, however, not only geometrically identical, but can, for example, also be identical in terms of their surface materials. The measurement chambers can, for example, each have identical aerosol feed lines onto the deposition surfaces and, for example, also have identical suction structures. One requirement in connection therewith is that each of these identical aerosol feed lines be supplied by the same superfine particle source. The goal of these embodiments is a comparable and most identical possible depositions of the same superfine particle quantities on each of the deposition surfaces.

If the exposure chambers differ from each other, for example, differences due to geometry or flow, the depositions are nevertheless fundamentally transferable. In connection therewith, deviations of the measured results and thus measurement errors can, where necessary, be minimized or corrected using fixed correction factors or variable correction functions (correlations) that can, for example, be determined empirically on the basis of comparative experiments.

The stated measures advantageously allow an online recording of the actual deposited superfine particle masses directly in the exposure system. Additional measurement units are not required. Conversion algorithms or modeling are thus eliminated as sources of inaccuracies or sources of errors. Owing to the utilization of a direct measurement concept, the device is thus particularly reliable, simple in construction, and thus cost-effective. A chemical or radioactive labeling of the aerosol or of the superfine particles for the purposes of a quantitative detection is not necessary.

The present invention and embodiments thereof will, by way of example, be more particularly described below on the basis of the drawings.

FIG. 1 shows an exemplary arrangement of six exposure chambers 1 for the throughflow of an aerosol in a common housing 2. The geometries of the throughflow volumes for the aerosol can, for example, be identical for all six exposure chambers 1. In the example, five of the six exposure chambers 1 are each provided with a transwell insert 3 as deposition surface 4 (cell culture surface on, for example, a polycarbonate membrane), whereas the deposition surface 4 in the sixth exposure chamber 1 is arranged on a piezoelectric crystal 5 as sensor of a quartz crystal microbalance. The deposition surface can, for example, be directly formed by the surface or the electrode of the piezoelectric crystal 5. FIG. 1 also contains a line indicated by A-A as sectional plane for the representation shown in FIG. 2.

Figure 2:
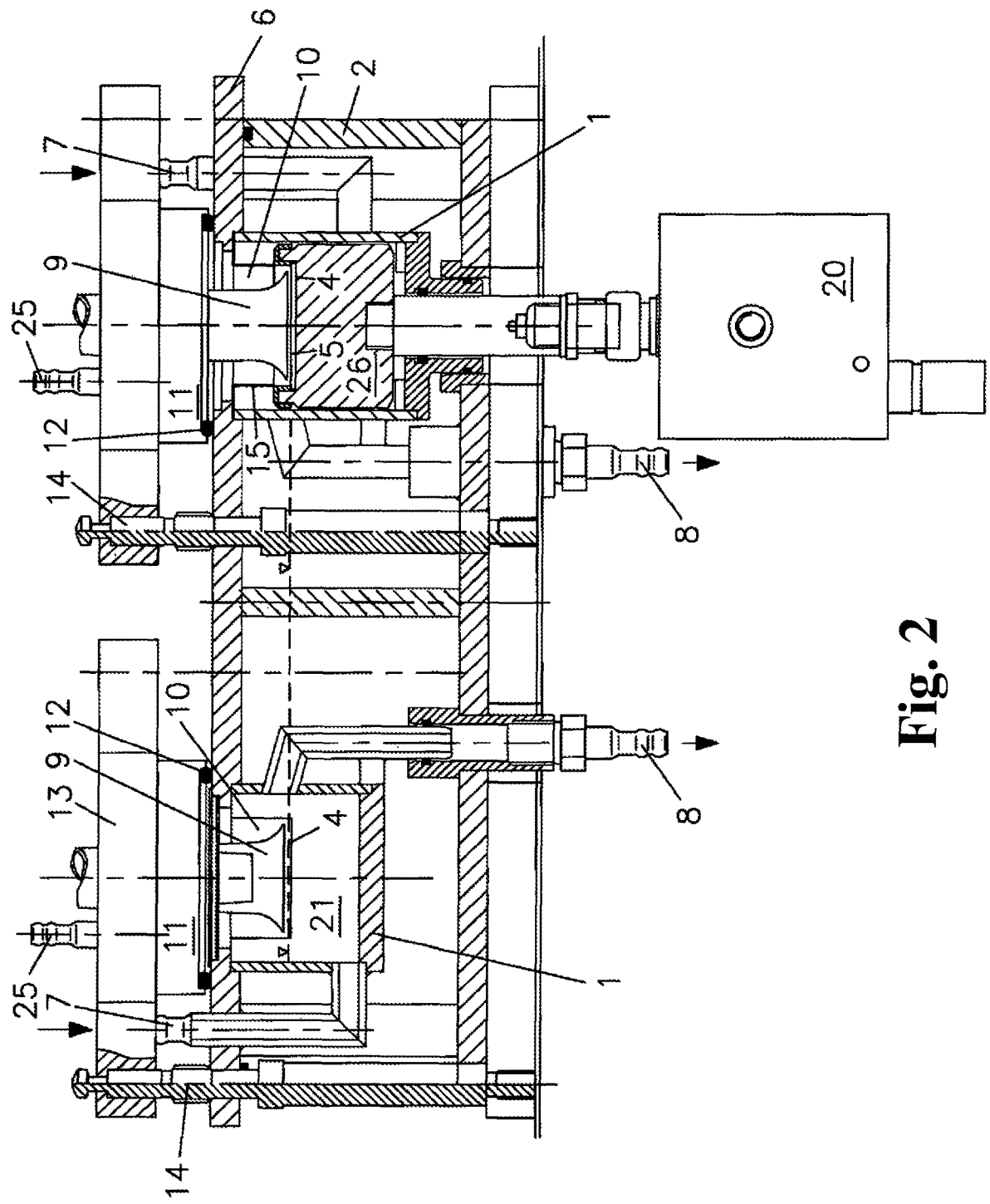

The overview views of the arrangement of the components as per FIGS. 1 and 2 are similar in structure to the prior art described in DE 10 2007 013 938 A1. The modifications are elucidated on the basis of the detailed representations as per FIGS. 3-4 and 6-7.

The sectional representation as per FIG. 2 discloses the topographic arrangement of two exposure chambers 1 arranged on the sectional plane A-A, wherein the exposure chamber 1 arranged on the right and provided with the aforementioned piezoelectric crystal 5 on an additional mass 26 as support below the deposition surface 4 as quartz crystal microbalance is designed for the measurement of superfine particle masses. The piezoelectric crystal 5 is inserted into an indentation of the mass 26 and is pressed from below against a ring-nut screw connection by springs integrated in the mass 26 that are not depicted further. The springs simultaneously serve for the electrical contacting of the electrodes of the piezoelectric crystal 5. Mass and ring-nut screw connection can, for example, then be made of an electrical insulator, such as plastic, for example, Teflon™.

The ring-nut screw connection, together with a collar 15 positioned thereon, geometrically delimits the throughflow volumes, especially in the region of the suction volume 10, in the geometric manner of the lateral vertical flanks of the transwell insert 3 in the exposure chamber 1 arranged on the left. In any case, the throughflow volumes are geometrically matched, are delimited by walls and fluid guides of the same topographies, for example, also by the same material surfaces, and are as identical as possible. An oscillator 20 controls the quartz crystal microbalance and records measurement data of the quartz crystal microbalance.

The exposure chambers 1 can, for example, be inserted from above into openings of a cover plate 6 of the housing 2 and arranged in parallel. If they are not provided with a piezoelectric crystal 5, they each have an inflow 7 and an outflow 8 for a nutrient medium for, in each case, a nutrient medium volume 21 below the deposition surfaces for the sustenance of the cell cultures forming the deposition surfaces. The outflow for nutrient medium 8 is arranged in the exposure chamber 1 so that it forms an outflow edge providing a constant fill level of the nutrient medium in the nutrient medium volume 21 and thus constantly providing that the cell culture is wetted and thus sustained from below.

FIG. 2 admittedly shows one inflow for nutrient medium 7 and one outflow for nutrient medium 8 for each of the exposure chambers 1 depicted, though the right-hand exposure chamber 1 with piezoelectric crystal 5 does not itself have these, but depicts the inflow for nutrient medium 7 and the outflow for nutrient medium 8 for the exposure chamber 1 behind it without piezoelectric crystal 1 (compare to FIG. 1).

The exposure chamber 1 with piezoelectric crystal as per FIG. 1 does not have a nutrient medium volume 21. The space requirement intended therefor is needed for the arrangement of the mass 26. The deposition surfaces 4 on the piezoelectric crystal 5 are thus also not accessible for a nutrient medium from below. For this reason, the deposition surfaces 1 on the piezoelectric crystal 5 consist, for example, of a low-damping material having a surface topography corresponding to that of a cell culture surface.

Each exposure chamber 1 also has an aerosol feed line 9 opening into it from above. The aerosol feed lines 9 conduct the aerosol stream across the deposition surfaces 4 and cause a local immission on the deposition surfaces, for example, proceeding from the center of the deposition surface 4, for example, evenly outwardly distributed in a radial manner. From the deposition surface 4 in turn, the aerosol stream is carried away and diverted by a suction volume 10 opening out into the annular channel 22 (compare sectional representation in FIGS. 3 and 4). The suction structure can, for example, comprise an annular channel 22 having an aerosol suction line 25 and a multiplicity of apertures (connection channels 18) for the suction volume 10 in the lid 11 around the deposition area for the purposes of radial suction of the aerosol stream. The deposition surface 4, aerosol feed line 9 and suction volume 10 are designed in an axis-symmetrical manner and arranged concentrically.

The deposition surfaces 4 of all the exposure chambers 1 extend on a plane parallel to the cover plate 6 and are, after raising of a lid 11 and of the aerosol feed line 9 for each exposure chamber 1, also accessible from above through the openings of the cover plate 6. To avoid an aerosol sidestream, the exposure chambers 1 are sealed at the top via, in each case, a sealing ring 12 between lid 11 and cover plate 6. The lids 11 are pressed onto the exposure chambers 1 via a pressure plate 13. The pressure plate 13 is guided on collar pins 14 inserted into the housing 2 and fixed in position via quick-release fasteners (which are not shown in the drawings).

FIGS. 3-4 and 6-7 reproduce in detail the sectional representations of the modified exposure chambers 1 shown in FIG. 2. In the design depicted, the exposure chambers 1 each have a grid 27 parallel over the deposition surfaces 4, which grids 27 span the entire outlet region 17 of the respective aerosol feed line 9.

Figure 3:
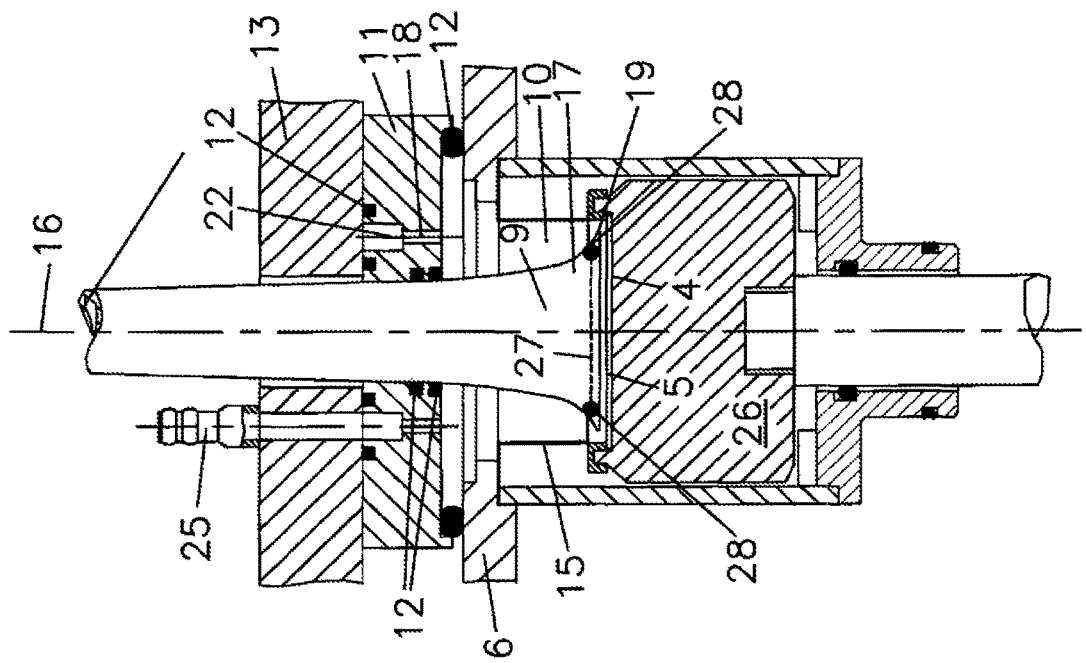
Figure 6:
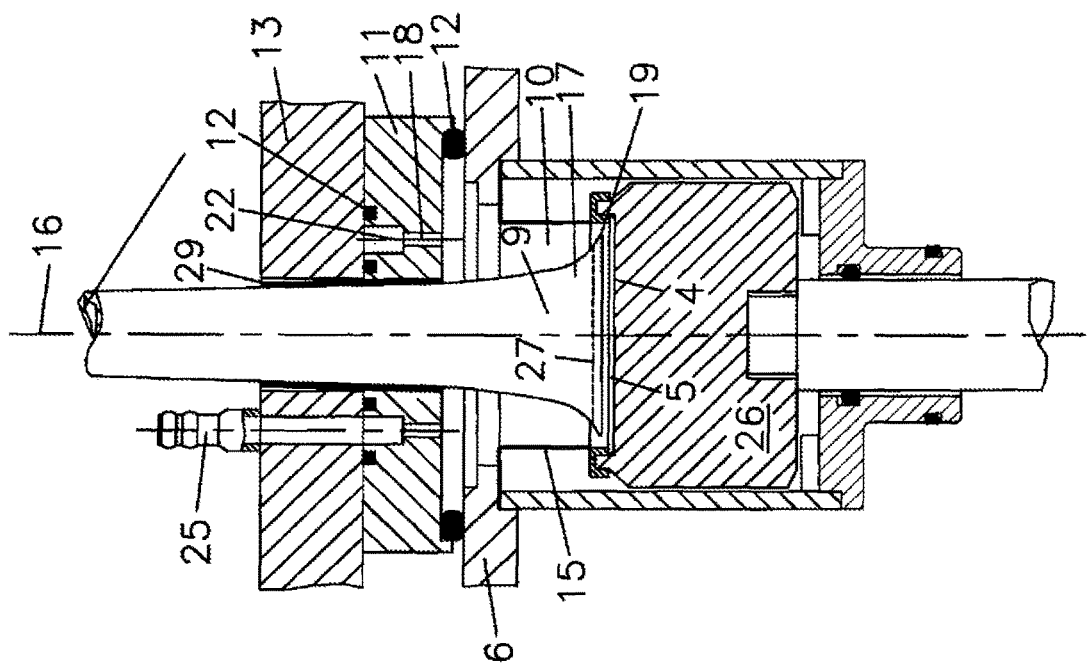

FIGS. 3 and 6 each show an exposure chamber without a microbalance. The deposition surface 4 extends in each case on the base region of the transwell insert 3, which is inserted into the exposure chamber 1 from above and centered and held by a beaker edge which is bent outward and engages under the lid 11. The inflow for nutrient medium 7 opens into the nutrient medium volume 21 below the deposition surface (i.e., the cell cultures), wets there the entire deposition surface 4 from below, and leaves the volume via the outflow for nutrient medium 8. The superfine particle masses are conducted from above as aerosol onto the deposition surface 4 through the aerosol feed line 9 arranged centrally around the axis of symmetry 16. The interior of the transwell insert 3 outside the outlet region 17 of the aerosol feed line 9, which outlet region 17 increasingly widens in a downward manner, forms the suction volume 10 arranged concentrically in an annular manner around the outlet region 17, comprising a multiplicity of connection channels 18 which are arranged concentrically around the aerosol feed line 9 and open out into the annular channel system 22. In this connection, the outlet region 17 spreads conically in a downward manner or, as depicted, for example, in a trumpet-shaped manner and forms in its entire circumference with the deposition surface 4 a circumferential annular gap 19 of constant width.

Figure 4:
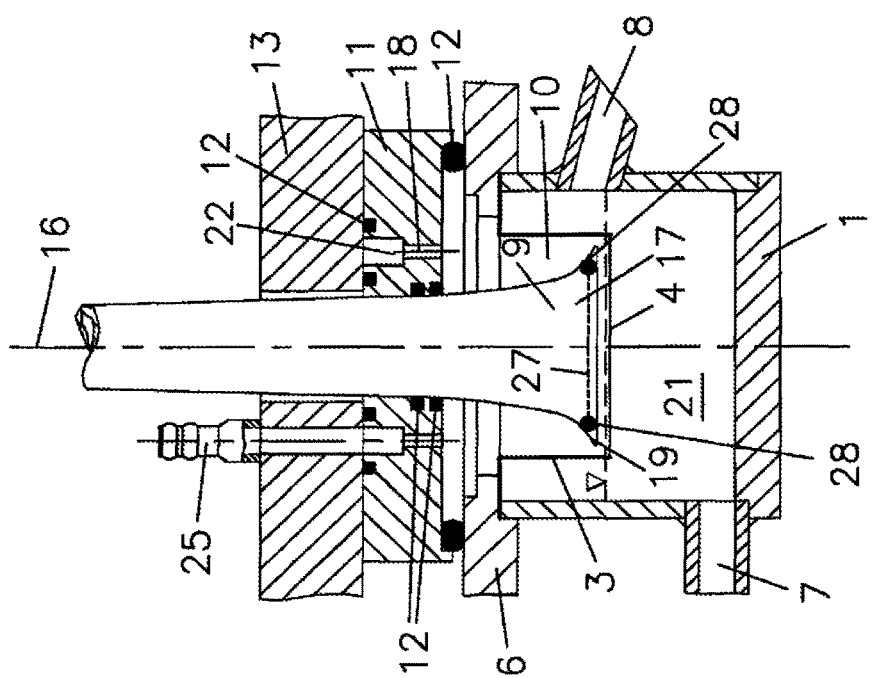
Figure 7:
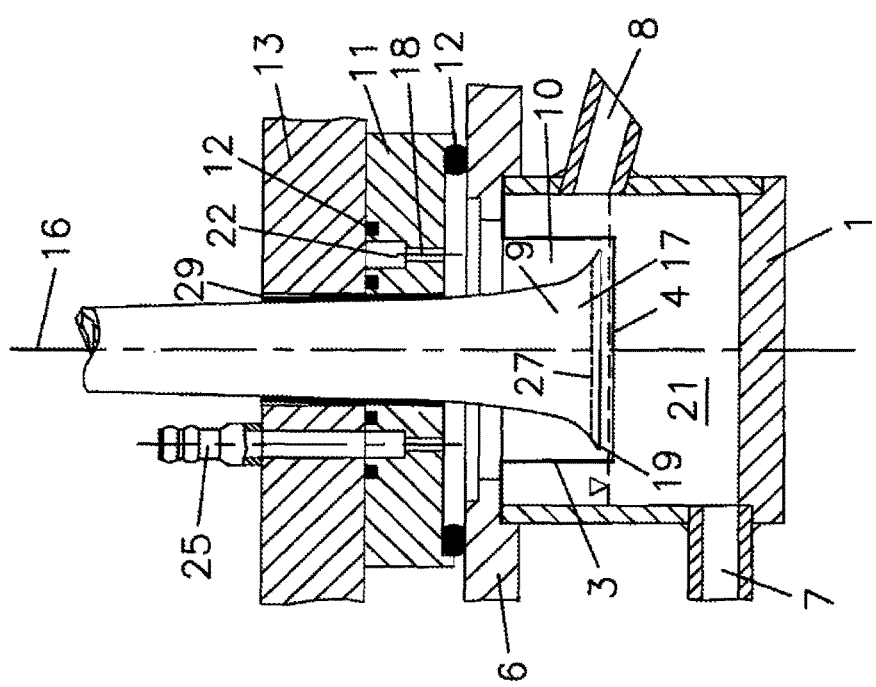

FIGS. 4 and 7 each show an exposure chamber provided with a piezoelectric crystal 5 as sensor of a quartz crystal microbalance. In terms of its structure, dimensions and operating principle, the region above the deposition surface 4 is identical to the aforementioned exposure chamber 1 without microbalance that is shown in FIGS. 3 and 6. The deposition surface 4 can, for example, be formed by the surface of the piezoelectric crystal 5, which in turn fills out the volume below the deposition surface 4 and is connected to the oscillator 20 from below (compare to FIG. 2).

In this connection, FIGS. 3 and 4 represent a design in which a potential having a potential difference of at least 200 volts, for example, the aforementioned potential differences, in relation to the potential of the deposition surface 4 is present only at each grid 27. The grid 27 is held in the aerosol feed line 9 by an electrically insulating ring 28 which is composed, for example, of a plastic, elastomer or a glass.

The grid 27 can, for example, be electrically connected via a high-voltage cable, which can, for example, be inserted above the pressure plate 13 into the aerosol feed line 9 via an insulated high-voltage bushing and is guided downward in the bushing to the grid 27.

Figure 5:
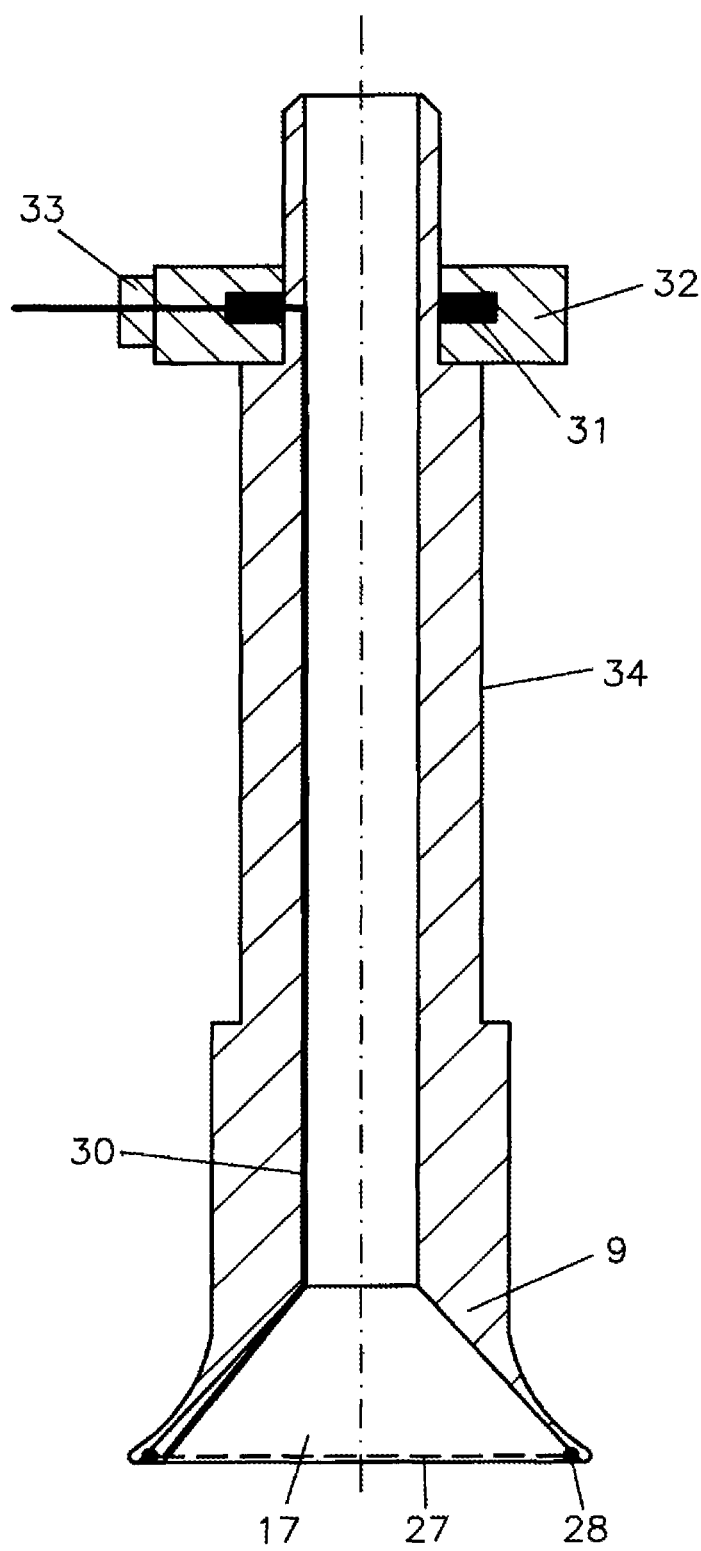

FIG. 5 shows an embodiment with a trumpet-shaped aerosol feed line 9 composed of electrically grounded stainless steel with the grid 27 composed of steel as an attachment at the aerosol exit at outlet region 17. Inserted between aerosol feed line 9 and steel grid 27 is an insulating ring 28 composed of polypropylene or Teflon™. The insulating ring 28 prevents a short circuit between the aerosol feed line 9, which is connected to ground potential and which can, for example, also be electrically connected to the deposition surface 4, and grid 27, which is conducting high voltage. The grid 27 can, for example, be supplied with high voltage through an insulated cable 30 in a groove on the inner side of the aerosol feed line 9 across the insulating ring 28 toward the grid 27, which insulated cable 30 is insulated until just before the grid 27. At the upper end of the aerosol feed line 9, the stranded wire of the insulated cable 30 contacts a circumferential ring 31 in a screw-on sleeve 32, at which there is situated a plug connection 33 for connection to the high-voltage supply (which is not further shown in the drawings). Although it would be easier to produce a groove alternatively on the outer side, this involves the risk of there subsequently being complications in the tightness of the exposure chamber in the housing of the device (especially between the pressure plate 13 or lid 11 and aerosol feed line 9 at the sealing surface 34), since the stranded wire in the groove causes an interruption in the sealing surface 34 of the sealing ring 12 (compare FIGS. 3 and 4).

By contrast, FIGS. 6 and 7 show designs in which the grid 27 is connected in an electrically conductive manner to the aerosol feed line 9. A potential having a potential difference of at least 200 volts, for example, the aforementioned potential differences, in relation to the potential of the deposition surfaces 4 is present on each combination of grid 27 and aerosol feed line 9. In the case of an electrically conductive aerosol feed line 9, this requires in turn an electrical, insulating and imperatively sealing mounting of the aerosol feed line 9 in the housing 2 of the device, as depicted by way of example by an insulation sleeve 29, for example, composed of a plastic or an elastomer.

An embodiment of the last-mentioned designs provides an aerosol feed line 9 having an electrically nonconductive inner surface, in which an electrically conductive tubular insert with grid 27 has been inserted, which insert extends in the aerosol feed line 9 from the outlet region 17, i.e., the position of the grid 27, to beyond the device and is connected there to a high-voltage supply via a high-voltage supply, as described FIG. 5. If the insert is provided with insulation away from the grid 27, this gives an embodiment of the designs described in FIGS. 3 and 4. If the entire tubular insert with grid 27 is inserted without insulation in the aerosol feed line 9, the embodiment corresponds to the designs described in FIGS. 6 and 7.

Grid 27 and deposition surface 4 form the electrodes for forming an electrical field. If these are arranged in parallel, a homogeneous electrical field forms over the entire extent of the grid 27 and of the deposition surface 4.

The following is to be observed when designing the device, especially the electrical contacts and fields:
- Avoidance of a short circuit between aerosol feed line 9 and lid 11; the lid 11 is to remain grounded.
- No open contacts with the high voltage (comprising the aforementioned intervals of, for example, 200 to 10 000 volts, for example, in the kV range).
- Optimally no change in the external geometry, meaning that a module comprising aerosol feed line 9 with grid 27 and deposition surface 4 with or without piezoelectric crystal 5 keeps its variable insertability in all positions.
- Tightness between lid 11 and aerosol feed line 9.
- Avoidance of large areas of electrostatically chargeable materials, such as Teflon™, so as not to cause any additional losses. This means that, for example, a Teflon™ aerosol feed line 9 is disadvantageous in the absence of further measures for diverting electric charges since the aerosols would otherwise already be altered between grid 27 and the deposition surface 4 or the electrode of the piezoelectric crystal 5 and would influence the result when measuring deposition.

Deposition of particle fractions can also be selectively influenced by a temperature difference between the particles in the aerosol and the deposition surfaces. For example, heating the deposition surface makes it possible to more easily vaporize certain fractions on the deposition surfaces. The temperature also significantly influences the dynamics of the physical, chemical and biological interactions between deposited particles and deposition surfaces and thus the deposition kinetics of individual particle fractions in a selective manner.

Alternative means for cooling the deposition surface and/or for heating the particles in the aerosol (e.g., via a device upstream of the aerosol feed line) bring about warmer particle masses flowing over a colder deposition surface. This means that gaseous constituents also, for example, condense on the deposition surface.

If the device is utilized for the in vitro analyses, as mentioned above, of superfine dust depositions (dust, pharmaceuticals, drugs, other active ingredients, spores, viruses or bacteria, etc.) or of biochemical or biophysical interactions on bioassays, i.e., on biological or biologically active surfaces, the deposition surfaces can, for example, consist of a biofilm or of a cell culture.

To provide a constant temperature, for example, of 37° C., for the aforementioned in vitro analyses, such as for toxicological applications, for example, in all exposure chambers, it is possible to flood the housing with a temperature-control medium, for example, water or oil, via a temperature-control inflow 23 and a temperature-control outflow 24 (compare FIG. 1). The temperature-control medium fills the internal volume of the housing 2, with a, for example, selective temperature control of the deposition surfaces 4 (indirectly via the nutrient medium in the nutrient medium volume 21 or the mass 26) being effected by setting the liquid level of the temperature-control medium, for example, to the height of the deposition surfaces 4 (compare dashed horizontal line in FIG. 2).

The present invention is not limited to embodiments described herein; reference should be had to the appended claims.

LIST OF REFERENCE SIGNS

1 Exposure chamber
2 Housing
3 Transwell insert
4 Deposition surface
5 Piezoelectric crystal
6 Cover plate
7 Inflow for nutrient medium
8 Outflow for nutrient medium
9 Aerosol feed line
10 Suction volume
11 Lid
12 Sealing ring
13 Pressure plate
14 Collar pins
15 Collar
16 Axis of symmetry
17 Outlet region
18 Connection channel
19 Annular gap
20 Oscillator
21 Nutrient media volume
22 Annular channel
23 Temperature-control inflow
24 Temperature-control outflow
25 Aerosol suction line
26 Mass
27 Grid
28 Insulation ring
29 Insulation sleeve
30 Insulated cable
31 Circumferential ring
32 Sleeve
33 Plug connection
34 Sealing surface

What is claimed is:

1. A device for measuring a mass of superfine particles, the device comprising:
an exposure system comprising at least two measurement chambers which have an identical geometry, each of the at least two measurement chambers comprising,
a deposition surface for the superfine particles,
an aerosol feed line directed to each deposition surface, the aerosol feed line comprising an outlet region for feeding an aerosol onto the deposition surface,
a means for generating a potential difference between the superfine particles in the aerosol and the deposition surface, and
a grid arranged above the deposition surface, the grid being configured to completely span the outlet region,
wherein,
the outlet region comprises a widened outlet cross section which is configured to have a constant distance from the deposition surface over its entire circumference so as to form a circumferential gap nozzle and so that a suction volume is arranged concentrically around the aerosol feed line, and
at least one deposition surface is arranged on a piezoelectric crystal as a superfine balance,
wherein,
a first potential corresponding to a ground potential is present at each deposition surface, and
a second potential having a potential difference of at least 200 V in relation to the first potential is present at each grid so that an electrical field spreads between a respective grid and a respective deposition surface.

2. The device as recited in claim 1, wherein at least one deposition surface is provided which is not arranged on the piezoelectric crystal.

3. The device as recited in claim 2, wherein the at least one deposition surface which is not arranged on the piezoelectric crystal is formed by a biofilm or by a cell culture.

4. The device as recited in claim 1, wherein the means for generating a potential difference between the superfine particles in the aerosol and the deposition surface comprises a device arranged upstream of the aerosol feed line, the device being configured to ionize the superfine particles in the aerosol.

5. The device as recited in claim 1, wherein the respective grid is arranged in parallel to the respective deposition surface.

6. The device as recited in claim 1, wherein a potential of a respective aerosol feed line is present at each grid.

7. The device as recited in claim 1, wherein each aerosol feed line is configured to provide a deflection of the aerosol over the respective deposition surface.

8. The device as recited in claim 1, wherein the exposure system further comprises a suction volume arranged around each aerosol feed line.

9. The device as recited in claim 1, wherein the outlet region is arranged to be rotationally symmetric around an axis of symmetry and to spread in a trumpet-shaped manner or in a conical manner.

10. The device as recited in claim 1, further comprising a means to generate a temperature difference between the superfine particles in the aerosol and the deposition surface.

11. The device as recited in claim 10, wherein the means to generate a temperature difference comprises at least one of a cooling unit for the deposition surface and a heating device for the superfine particles in the aerosol, the heating device being arranged upstream of the aerosol feed line.

* * * * *